(12) United States Patent
Haapalinna et al.

(10) Patent No.: US 6,495,584 B1
(45) Date of Patent: Dec. 17, 2002

(54) USE OF 3-(1H-IMIDAZOL-4-YLMETHYL)-INDAN-5-OL IN THE MANUFACTURE OF A MEDICAMENT FOR INTRASPINAL, INTRATHECAL OR EPIDURAL ADMINISTRATION

(75) Inventors: Antti Haapalinna, Turku (FI); Jyrki Lehtimäki, Sauvo (FI); Tiina Leino, Piikkiö (FI); Timo Viitamaa, Turku (FI); Raimo Virtanen, Rusko (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/787,886

(22) PCT Filed: Sep. 27, 1999

(86) PCT No.: PCT/FI99/00793

§ 371 (c)(1),
(2), (4) Date: Mar. 26, 2001

(87) PCT Pub. No.: WO00/18400

PCT Pub. Date: Apr. 6, 2000

Related U.S. Application Data

(60) Provisional application No. 60/101,986, filed on Sep. 28, 1998.

(51) Int. Cl.$^7$ ............................................. A61K 31/415
(52) U.S. Cl. ........................................................ 514/399
(58) Field of Search ........................................... 514/399

(56) References Cited

U.S. PATENT DOCUMENTS 5,801,188 A    9/1998   Hassenbusch, III et al.

6,313,311 B1   11/2001  Karjalainen et al.

FOREIGN PATENT DOCUMENTS

EP    0 424 059 A1    4/1991
WO    WO 97/12874    4/1997

OTHER PUBLICATIONS

Peter Staats et al., "Future Directions for Intrathecal Therapies", Progress in Anesthesiology, pp. 367–382.

Laitin et al., "$\alpha_2$–agonists for analgesia", Emerging Drugs, vol. 18, pp. 377–389 (1996).

James Eisenach, "Alpha–2 agonists and analgesia", Exp. Opin. Invest. Drugs, vol. 3 (10), pp. 1005–1010 (1994).

Tony Yasksh et al., "Chronic Catheterization of the Spinal Subarachnoid Space", Physiology & Behavior, vol. 17, pp. 1031–1036 (1976).

Co–pending U.S. patent application No. 10/018,545, § 371 filing date of Mar. 8, 2002.

*Primary Examiner*—Russell Travers
*Assistant Examiner*—San-ming Hui
(74) *Attorney, Agent, or Firm*—Finnegan, Henderson, Farabow, Garrett & Dunner L.L.P.

(57) ABSTRACT

The present invention relates to a method for obtaining analgesia by administering 3-(1H-imidazol-4-ylmethyl)-indan-5-ol, its enetiomer or pharmaceutically acceptable ester or salt thereof to a mammal intraspinally, 3-(1H-imidazol-4-ylmethyl)-indan-5-ol, its enantiomer or a pharmaceutically acceptable ester or salt thereof can be administered intraspinally to a mammal obtaining analgesia without side-effects, such as sedation. The present invention also relates to a method for using the drug as an adjunct to anaesthesia by administering it intraspinally.

24 Claims, 2 Drawing Sheets

USE OF 3-(1H-IMIDAZOL-4-YLMETHYL)-INDAN-5-OL IN THE MANUFACTURE OF A MEDICAMENT FOR INTRASPINAL, INTRATHECAL OR EPIDURAL ADMINISTRATION

This application claims the benefit of priority under 35 U.C.S. 119(e) to U.S. Provisional Application No. 60/101,986, filed on Sep. 28, 1998.

This application is a national stage filing of PCT International Application No. PCT/F199/00793, filed on Sep. 27, 1999, which published in the English language.

BACKGROUND OF THE INVENTION

The present invention relates to a new method of administering 3-(1H-imidazol-4-ylmethyl)-indan-5-ol, its enantiomer or a pharmaceutically acceptable ester or salt thereof. Accordingly, the present invention relates to an intraspinal administration of 3-(1H-imidazol-4-ylmethyl)-indan-5-ol, its enantiomer or a pharmaceutically acceptable ester or salt thereof to obtain analgesia. The intraspinal administration is intented to include epidural, intrathecal and intrarrhachidian administration. Accordingly, the present invention relates to a method for obtaining analgesia in a mammal by administering 3-(1H-imidazol-4-ylmethyl)-indan-5-ol, its enantiomer or a pharmaceutically acceptable ester or salt thereof intraspinally. Particularly, the present invention relates to an intraspinal administration of 3-(1H-imidazol-4-ylmethyl)-indan-5-ol, its enantiomer or a pharmaceutically acceptable ester or salt thereof for obtaining analgesia without sedation. Further, the present invention relates to a method of using 3-(1H-imidazol-4-ylmethyl)-indan-5-ol, its enantiomer or a pharmaceutically acceptable ester or salt thereof as an adjunct to anaesthesia by administering the drug intraspinally. The present invention also relates to a method for treating a mammal by administering 3-(1H-imidazol-4-ylmethyl)-indan-5-ol, its enantiomer or a pharmaceutically acceptable ester or salt thereof intraspinally. Further, the present invention relates to the use of 3-(1H-imidazol-4-ylmethyl)-indan-5-ol, its enantiomer or a pharmaceutically acceptable ester or salt in the manufacture of a medicament for intraspinal administration.

3-(1H-Imidazol-4-ylmethyl)-indan-5-ol has the following formula:

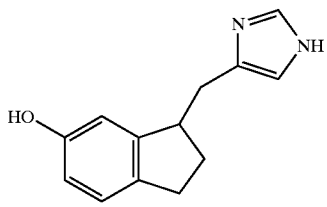

3-(1H-Imidazol-4-ylmethyl)-indan-5-ol is described in WO 97/12874 as an $\alpha_2$-receptor agonist useful in the treatment of hypertension, glaucoma, migraine, diarrhea, ischemia, addiction to chemical substances, anxiety, especially preoperative anxiety, and different neurological, musculosketal, psychiatric and cognition disorders as well as a sedative and an analgesic agent, nasal decongestant, and as an adjunct to anaesthesia. Enteral, topical, and parenteral routes of administration and a method for producing the compound are discussed in WO 97/12874.

Opioids, especially morphine, are routinely used for intraspinal and epidural administration to give analgesia. However, according to Eisenach J. E. (Exp. Opin. Invest. Drugs 3(10), 1994, 1005–1010) the major concern limiting the use of intraspinal morphine is the 0.1 to 0.2% incidence of severe respiratory depression, occurring six to twelve hours after injection.

$\alpha_2$-Receptor agonists are being evaluated for obtaining analgesia by administering them intrathecally or epidurally. At the moment, the only $\alpha_2$-receptor agonist approved by the FDA for obtaining analgesia by epidural administration is clonidine (DURACLONO®). According to Laitin S. & Wallac M. ("$\alpha_2$-agonists for analgesia", Emerging Drugs 1996, Chapter Eighteen, 377–399, Ashley Publications Ltd.) the lipid solubility of clonidine results in significant systemic absorption when administered epidurally. This results in significant systemic side-effects, such as, sedation and hypotension. It is suggested that agents with lower lipid solubility may be advantageous. Also, Eisenach J. C. in Exp. Opin. Invest. Drugs 3(10), 1994, 1005–1010, states that injectable $\alpha_2$-agonist drug development would logically focus on compounds of low lipophilicity. Increasing lipophilicity is associated with more rapid and extensive absorption into the vasculature and redistribution in the body, which for $\alpha_2$-agonists could lead to a greater likelihood or intensity of sedative and haemodynamic side-effects.

Further, Staats P. S. & Mitchell V. D. (Progr. Anesthesiol. 11(19), 1997, 367–382) state that, although clonidine has been demonstrated to be a powerful analgesic agent, the clinical use of intrathecal clonidine has been limited by side-effects, primarily hypotension and bradycardia.

SUMMARY OF THE INVENTION

Applicants have discovered that 3-(1H-imidazol-4-ylmethyl)-indan-5-ol, its enantiomer or a pharmaceutically acceptable ester or salt thereof is an ideal agent to be administered to a mammal intraspinally for obtaining analgesia. Accordingly, an object of the invention is to provide a method for obtaining analgesia by administering 3-(1H-imidazol-4-ylmethyl)-indan-5-ol, its enantiomer or a pharmaceutically acceptable ester or salt thereof to a mammal intraspinally in an amount sufficient to give the desired therapeutic effect. Applicants surprisingly discovered that 3-(1H-imidazol-4-ylmethyl)-indan-5-ol, its enantiomer or a pharmaceutically acceptable ester or salt thereof can be administered intraspinally to a mammal obtaining analgesia without side-effects, such as sedation. This is surprising because 3-(1H-imidazol-4-ylmethyl)-indan-5-ol has a considerable higher lipophilicity when compared to clonidine at physiological pH. Because of the higher lipophilicity it would have been expected that 3-(1H-imidazol-4-ylmethyl)-indan-5-ol would cause also the systemic adverse effects when administered intraspinally as clonidine does.

It should be noted that the method for obtaining analgesia in a mammal encompasses all of the potential conditions that require the treatment of pain, e.g., intraoperative pain; postoperative pain; obstetric pain; chronic pain, such as cancer-related pain and neuropathic pain; and spastic paraplegia. Further, it should be noted that intraspinal administration is intented to include epidural, intrathecal (i.e., within the spinal subarachnoid or subdural space), and intrarrhachidian administration.

An object of the invention is also to provide a method for treating a mammal by administering 3-(1H-imidazol-4-ylmethyl)-indan-5-ol, its enantiomer or a pharnmaceutically acceptable ester or salt thereof intraspinally for a time sufficient to give the therapeutic effect.

An aspect of the invention is also to provide a method of using 3-(1H-imidazol-4--ylmethyl)-indan-5-ol, its enantiomer or a pharmaceutically acceptable ester or salt thereof intraspinally as an adjunct to anaesthesia.

A further aspect of the invention relates to a use of 3-(1H-imidazol-4-ylmethyl)-indan-5-ol, its enantiomer or a pharmaceutically acceptable ester or salt thereof in the manufacture of a medicament for intraspinal administration.

In a further aspect, the invention relates to a use of 3-(1H-imidazol-4-ylmethyl)-indan-5-ol, its enantiomer or a pharmaceutically acceptable ester or salt thereof in an intraspinal administration to a mammal to obtain analgesia.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Figure 1:
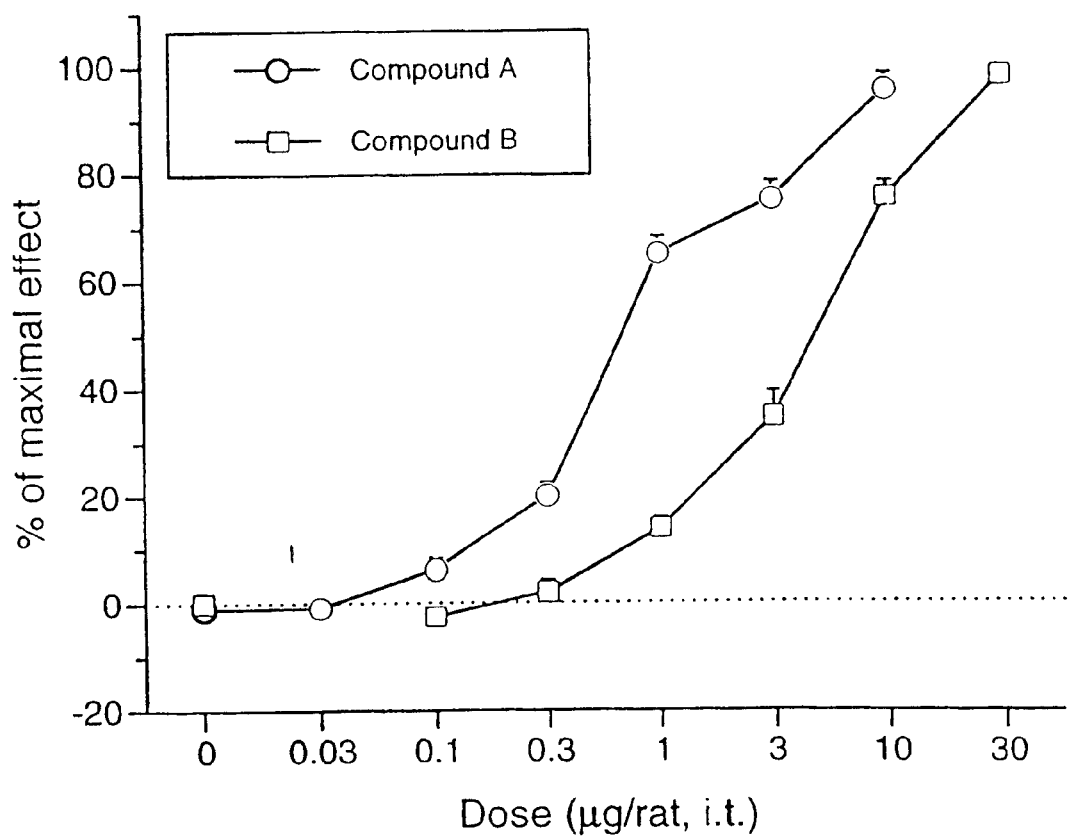
FIG. 1 shows the effect of 3-(1H-imidazol-4-ylmethyl)-indan-5-ol (Compound A) and clonidine (Compound B) on tail-flick analgesia.

Applicants have surprisingly discovered that 3-(1H-imidazol-4-ylmethyl)-indan-5-ol, its enantiomer or a pharmaceutically acceptable ester or salt thereof is effective for obtaining analgesia when administered intraspinally to a mammal. Particularly, it has been found that 3-(1H-imidazol-4-ylmethyl)-indan-5-ol, its enantiomer or a pharmaceutically acceptable ester or salt thereof can be administered intraspinally to a mammal for obtaining selective analgesia.

The method for obtaining analgesia in a mammal encompasses all of the potential conditions that require the treatment of pain, e.g., intraoperative pain; postoperative pain; obstetric pain; chronic pain, such as cancer-related pain and neuropathic pain; and spastic paraplegia.

Applicants surprisingly found that in spite of the considerably higher lipophilicity of 3-(1H-imidazol-4-ylmethyl)-indan-5-ol compared to clonidine at physiological pH, the drug seems to have an unexpectedly limited ability to move across the blood brain barrier or to the periphery after being administered intraspinally. Because of the higher partition coefficient, i.e. logD, values compared to clonidine, it would have been expected that 3-(1H-imidazol-4-ylmethyl)-indan-5-ol would cause systemic adverse effects when administered intraspinally as clonidine does. To the contrary, applicants discovered that 3-(1H-imidazol-4-ylmethyl)-indan-5-ol is a safer and more viable drug than clonidine to be administered to a mammal intraspinally. Accordingly, for example, administering 3-(1H-imidazol-4-ylmethyl)-indan-5-ol intrathecally at an analgesic dose was found not to induce sedation in a rat as clonidine did (see Example 2, Table 2). Further, in regard to other common adverse effects known for $\alpha_2$-agonists, applicants found that, e.g., impairment of motor coordination, hypothermia and inhibition of gastrointestinal motility was induced by intrathecal 3-(1H-imidazol-4-ylmethyl)-indan-5-ol, or its enantiomers at a much higher dose than needed for analgesia. This is really exceptional when compared with the results received from the corresponding tests with clonidine.

Applicants also discovered that intraspinally administered 3-(1H-imidazol-4-ylmethyl)-indan-5-ol, or its enantiomers are selectively analgesic compared to other routes of administration. Accordingly, 3-(1H-imidazol-4-ylmethyl)-indan-5-ol is needed in approximately the same amount when administered subcutaneously or intrathecally to achieve sedation, but at least 142-times less is needed when administered intrathecally to achieve analgesia (see Example 3, Table 3).

Because 3-(1H-imidazol-4-ylmethyl)-indan-5-ol, its enantiomer or a pharmaceutically acceptable ester or salt thereof is so selectively analgesic when administered intraspinally, it is very useful as an adjunct to anaesthesia. Anaesthesia is a loss of sensation resulting from pharmacologic depression of nerve function wherein the ability to perceive pain and/or other functions is lost. On the other hand, in analgesia painful stimuli are so moderated that, though still perceived, they are no longer painful. When the drug is used as an adjunct to anaesthesia, less anaesthesia are needed, and possible dosing problems would be avoided. 3-(1H-imidazol-4-ylmethyl)-indan-5-ol, its enantiomer or a pharmaceutically acceptable ester or salt thereof can be administered into the spinal space, e.g., by an injection or a continuous infusion. The precise amount of the drug to be administered to a mammal intraspinally or epidurally is dependent on numerous factors known to one skilled in the art, such as, the type of mammal, the general condition of the patient, the condition to be treated, the desired duration of use, etc. The dose for a human can be from about 30 to 500 μg/patient, preferably about 50–200 μg/patient. The dose for smaller mammals, e.g., dogs and cats, can be about 1–100 μg/patient, preferably 3–30μg/patient.

One skilled in the art would recognize the dosage forms suitable in the method of the present invention. The injections or infusions may contain one or more diluents or carriers.

3-(1H-imidazol-4-ylmethyl)-indan-5-ol can be prepared, for example, as described in WO 97/12874. Accordingly, it can be prepared by heating a stirred mixture of 4-(6-methoxyindan-1-ylmethyl)-1H-imidazole hydrochloride (140 mg) and 48% hydrobromic acid (7 ml) under reflux for 45 minutes; cooling the reaction mixture; pouring the reaction mixture into water and making it basic with ammonium hydroxide solution; extracting the product into ethyl acetate; washing the ethyl acetate phase with water; drying it with sodium sulphate; and finally evaporating to dryness. The crude product can be converted, e.g., to its hydrochloride salt in ethyl acetate using dry hydrochloric acid. The melting point of the hydrochloride salt is 206–208° C. Other acid addition salts may be formed with inorganic and organic acids. Typical acid addition salts in addition to chlorides are bromides, sulfates, nitrates, phosphates, sulfonates, formates, tartrates, maleates, citrates, benzoates, salicylates, and ascorbates. Further, the hydroxy group can form esters and salts with alkali and alkaline earth metals. Typical esters include the lower alkyl esters, such as, the methyl, ethyl, and propyl esters.

The invention will be further clarified by the following examples, which are intended to be purely exemplary of the invention.

EXAMPLE 1

The experimental partition coefficients for 3-(1H-imidazol-4-ylmethyl)-indan-5-ol (compound A) and clonidine (compound B) were determined by the shake flash method. The hydrochloride salts of the above compounds were shaken for 90 minutes in a separatory funnel at room temperature with equal volumes (1:1, v/v) of an organic phase (water saturated 1-octanol) and an aqueous solution (0.1 M HCI or 67 mM phosphate buffer pH 7.4), separating the two phases. The quantitations of the amounts of the studied compounds were performed by the RP-HPLC (reverse phase high pressure liquid chromatography) technique. The detection wavelength was 282 nm for 3-(1H-imidazol-4-ylmethyl)-indan-5-ol and 272 nm for clonidine. As a mobile phase, methanol: 15 mM phosphate buffer pH2 at the ratio 50:50 (v/v) was used.

The partition coefficient (P) is a ratio of the equilibrium concentrations of a solute in a lipophilic environment (1-octanol) and water ($P=c_{oct}/c_{water}$). The logarithm of the partition coefficient (logP) is used as a lipophilicity parameter for a neutral molecule. D is the partition coefficient measured at a pH where the molecules are partly or totally ionized. The results, which are presented in Table 1, show that 3-(1H-imidazol-4-ylmethyl)-indan-5-ol is more lipophilic than clonidine, especially at a physiological pH (pH 7.4).

TABLE 1

Experimental partition coefficients for 3-(1H-imidazol-4-ylmethyl)-indan-5-ol (compound A) and clonidine (compound B) at pH 1 and pH 7.4.

| Compound | logD (pH 1) | logD (pH 7.4) |
|---|---|---|
| A | −0.69 | 1.91 |
| B | −1.02 | 0.73 |

EXAMPLE 2

The analgesic-potencies of 3-(1H-imidazol-4-ylmethyl)-indan-5-ol and clonidine were tested in vivo in rats after administering the water solutions of the hydrochloride salts of the drugs intrathecally (i.t.). There were 8 rats in each group tested. 3-(1H-imidazol-4-ylmethyl)-indan-5-ol hydrochloride was administered at 0.03, 0.1, 0.3, 1, 3, and 10 μg/animal i.t. and clonidine hydrochloride was administered at 0.1, 0.3, 1, 3, 10, and 30 μg/animal i.t. in the analgesia test. In the test measuring the sedative effects, 3-(1H-imidazol-4-ylmethyl)-indan-5-ol hydrochloride was administered at 1, 3, 10, and 30 μg/animal i.t. and clonidine hydrochloride was administered at 0.3, 1, 3, and 10 μg/animal i.t. The doses of the both compounds administered in the gastrointestinal motility test were 1, 3, 10, 30, and 100 μg/animal i.t. Water was used as a control.

Intrathecal Catheterization of the Animals

The rats (Sprague-Dawley, B&K, Sollentuna, Sweden) were anaesthetized by midazolam and fentanyl-fluanisone combination anaesthesia and then chronically catheterized according to the method described by Yaksh and Rudy (Physiology & Behaviour 17,1031–1036, 1976). Briefly, the atlanto-occipital membrane of the spine (directly below the skull) was incised. A polyethylene catheter (PE10 Intramedic, USA) filled with sterile saline was carefully and slowly pushed 8 cm into the spinal cavity. The end of the catheter is known to reach the close proximity of the lumbar enlargement of the spine. The location of the end of the catheter was tested by administering 0.5 mg lidocain approximately 3 days after catheterization. If both hindlegs were paralyzed, the rat was used in the drug tests.

Measurement of Analgesic and Other Pharmacological Activities

The analgesic activity and other pharmacological effects (sedative effect, impairment of motor coordination, hypothermic effect and inhibition of gastrointestinal motility) of 3-(1H-imidazol-4-ylmethyl)-indan-5-ol and clonidine after intrathecal administration were studied in rats as follows:

Analgesic Activity

Tail-flick analgesia was tested by a tail-flick analgesy meter (Ugo Basile, Italy). The analgesia testing was done no earlier than four days after the catheterization. The rats were always habituated to the immobilization chambers that were used in the analgesia measurements. The tail of the rat was outside the chamber and it was placed on the heating spot of the apparatus. Thus, the hot infrared beam would hit the tail. When the rat reacted and moved the tail away from the beam, the analgesy meter automatically measured the latency of the tail-withdrawal. The tail-flick measurement was always repeated three times, one after another, to diminish the effect of a possible unspecific reaction. The heating spot of the tail was moved slightly towards the end of the tail, so that the beam did not hit the same area of the tail within one measurement. The maximal latency (cut-off time) was set to 5 seconds in order to prevent burns of the tail. The predrug tail-flick latencies were first measured, and then the rats were administered 10 μl of the drug solution by a Hamilton syringe. Immediately thereafter the catheter was washed with 10 μl of sterile saline, and the tip was sealed by a lighter. The analgesia was tested after 30 minutes from the administration of the drug by measuring tail-flick analgesia as described above.

The tail-flick analgesia data were represented as MPE% values (maximum possible effect %). The tail-flick latencies (mean of three measurements) were calculated as MPE% values as follows: (postdrug latency−predrug latency)/(cut-off time−predrug latency)×100%. The dose-response curves were drawn of the MPE% values, and the dose was on a logarithmic scale (see FIG. 1). The $ED_{50}$ (the dose inducing 50% of the maximal effect) values of the dose-response graphs were determined by the Graph Pad Prism v. 1.03 (San Diego, USA) software.

Adverse Effect Evaluation

The effect on motor coordination was evaluated by a rotarod treadmill for rats (Ugo Basile, Italy). It consists of four drums (diameter of 70 mm) separated by five flanges. The drums were adjusted to rotate 4 revolutions per minute. The rod was rotated against the direction of the rat, so it had to walk forward to stay on the rod. The rats were first trained to stay on the rod for at least two minutes. If a rat was not able to fulfill this criteria, it was not used in the study. The selected animals were catheterized for testing of the effects of the drugs on the time they were able to stay on the drum.

Sedative effects (effects on motor activity) were measured in a polypropylene animal cage (38×22×15 cm) with a transparent polypropylene lid by Photobeam Activity System (PAS, Cage Rack, San Diego Instruments, San Diego, USA). The system consists of 16 separate enclosures connected to a computer control unit. There were three photobeams in each enclosure. The enclosures surrounded the cage at the height of 5 cm. The breaking of beams was counted as locomotor activity.

Effects on body temperature were measured by a digital thermometer (Ellab, Denmark) with a rectal probe.

Figure 2:
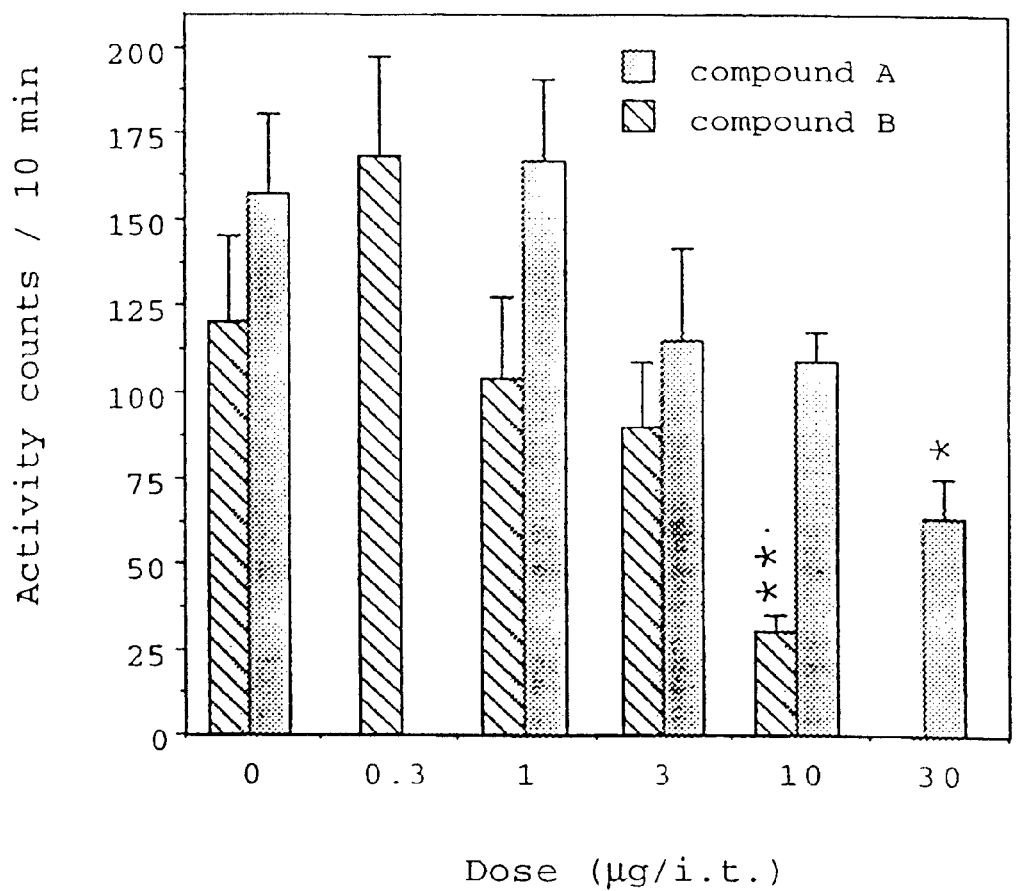
FIG. 2 shows the effect of 3-(1H-imidazol-4-ylmethyl)-indan-5-ol (Compound A) and clonidine (Compound B) on motor activity.

Fifteen minutes after the drug injection, the rat was placed on the rotarod apparatus, and the falling time was measured. After the rotarod measurement, the rat was placed into the motor activity measurement cage surrounded by the photobeam enclosures, and the activity was measured for 10 minutes. Immediately after the locomotor activity measurement (i.e. approximately after 30 min from administration), the core temperature was measured. The effect of 3-(1H-imidazol-4-ylmethyl)-indan-5-ol and clonidine on motor activity is shown as a bar graph in FIG. 2. The p values were calculated for the 10 $\mu$g and 30 $\mu$g doses; "*" signifies a statistical signifigance of p<0.05 and "**" signifies a statistical signifigance of p<0.01 in the Wilcoxon Signed Rank Test for control response. The dose-response curves were drawn on a logarithmic scale, and the $ED_{50}$ values were determined graphically from these.

Effects on gastrointestinal motility were measured in separate animals as follows (the charcoal propulsion test). The rats (8/group) were fasted overnight and were randomized according to the latin square design. 30 minutes after the administration of the drugs, a 10% charcoal suspension in 0.25% Na-carboxy-methylcellulose was administered perorally by a gavage. The rats were sacrificed after a further 30 minutes by $CO_2$ gas, their stomachs were opened, and their intestines were drawn carefully out. The distance of the charcoal suspension from the pylorus in the intestine was measured. The dose-response curves were drawn of the distance data (cm) and the dose was on a logarithmic scale. The $ED_{50}$ value of the dose-response graph was determined by the Graph Pad Prism v. 1.03 (San Diego, USA) software.

Results

The results from these pharmacological experiments are shown in Table 2. They show that 3-(1H-imidazol-4-ylmethyl)-indan-5-ol is clinically effective when administered intrathecally. It can be seen that 3-(1H-imidazol-4-ylmethyl)-indan-5-ol as well as clonidine had a potent analgesic effect after intrathecal administration. Surprisingly, 3-(1H-imidazol-4-ylmethyl)-indan-5-ol induced both supraspinally (sedation, impairment of motor coordination, hypothermia) or peripherally (inhibition of gastrointestinal motility) mediated side effects only after much higher doses than needed to induce significant analgesia. This is in contrast to clonidine, which induced all these effects already at the analgesic dose range.

These results indicate that, despite its high lipid solubility compared to clonidine (see the logD values in Example 1), 3-(1H-imidazol-4-ylmethyl)-indan-5-ol has a surprisingly limited ability to move upwards through the blood brain barrier to the brain or the periphery. Based on these results intraspinal 3-(1H-imidazol-4-ylmethyl)-indan-5-ol should have a specific analgesic effect without significant supraspinal or peripheral side effects in humans and other mammal.

TABLE 2

Potency of analgesic and other in vivo pharmacological effects of intrathecal 3-(1H-imidazol-4-ylmethyl)-indan-5-ol (compound A) and clonidine (compound B) in the rat.

| | | $ED_{50}$, g/rat | |
| Index | | compound A | compound B |
| --- | --- | --- | --- |
| A | Analgesia[1] | 0.7 | 6.4 |
| B | Sedation[2] | 30 | 5 |
| C | Loss of motor coordin.[3] | >30 | >10 |

TABLE 2-continued

Potency of analgesic and other in vivo pharmacological effects of intrathecal 3-(1H-imidazol-4-ylmethyl)-indan-5-ol (compound A) and clonidine (compound B) in the rat.

| | | $ED_{50}$, g/rat | |
| Index | | compound A | compound B |
| --- | --- | --- | --- |
| D | Hypothermia[4] | 10 | 4 |
| E | Inhib. of GI motility | 5.7 | 3.5 |
| Ratio | B/A | 42.9 | 0.8 |
| | C/A | >42.9 | >1.6 |
| | D/A | 14.3 | 0.6 |
| | E/A | 8.1 | 0.5 |

[1]tail-flick test
[2]decrease in spontaneous locomotor activity
[3]decrease in rotarod performance
[4]–1° C. in body temperature

EXAMPLE 3

The analgesic potencies and sedative effects of 3-(1H-imidazol-4-ylmethyl)-indan-5-ol were tested in vivo in rats after administering the water solution of the hydrochloride salt of the drug intravenously and subcutaneously. These results are compared with the analgesia and sedation results obtained in Example 2.

The analgesic activity and sedative effect after intravenous (to the tail vein) and subcutaneous administration were studied according to the methods described in Example 2. The results are shown in Table 3. They show that 3-(1H-imidazol-4-ylmethyl)-indan-5-ol is needed in an at least 14-times greater dose when administered intravenously and in an at least 142-times greater dose when administered subcutaneously than the amount of the drug needed when administered intrathecally in order to achieve the analgesic effect. On the other hand, there is not much difference in the amounts needed to give a sedative effect when administered subcutaneously or intrathecally.

TABLE 3

Potency of analgesic and sedative effects of intravenous (iv), subcutaneous (sc), and intrathecal (it) 3-(1H-imidazol-4-ylmethyl)-indan-5-ol in the rat.

| | | $ED_{50}$, $\mu$g/kg | | |
| Index | | iv | sc | it |
| --- | --- | --- | --- | --- |
| A | Analgesia | >30 | >300 | 2.1* |
| B | Sedation | | 80 | 90* |

*the corresponding result $\mu$g/rat from Table 2 multiplied by 3 to get $\mu$g/kg Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The references discussed herein are specifically incorporated by reference in their entirety.

What is claimed is:

1. A method for obtaining analgesia in a mammal, comprising intraspinally administering to the mammal in need thereof an effective amount of 3-(1H-imidazol-4-ylmethyl)-indan-5-ol, in any enantiomeric form, or a pharmaceutically acceptable ester or salt thereof.

2. The method according to claim 1, wherein 3-(1H-imidazol-4-ylmethyl)-indan-5-ol hydrochloride is administered.

3. The method according to claim 1, wherein the 3-(1H-imidazol-4-ylmethyl)-indan-5-ol or pharmaceutically acceptable ester or salt thereof is administered intrathecally.

4. The method according to claim 1, wherein the 3-(1H-imidazol-4-ylmethyl)-indan-5-ol or pharmaceutically acceptable ester or salt thereof is administered epidurally.

5. The method according to claim 1, wherein the mammal is a human.

6. The method according to claim 5, which comprises administering from about 30 to about 500 µg of the 3-(1H-imidazol-4-ylmethyl)-indan-5-ol, in any enantiomeric form, or a pharmaceutically acceptable ester or salt thereof, to the mammal.

7. The method according to claim 6, which comprises administering from about 50 to about 200 µg of the 3-(1H-imidazol-4-ylmethyl)-indan-5-ol, in any enantiomeric form, or a pharmaceutically acceptable ester or salt thereof, to the mammal.

8. The method according to claim 1, wherein the mammal is a dog or a cat.

9. The method according to claim 8, which comprises administering from about 1 to about 100 µg of the 3-(1H-imidazol-4-ylmethyl)-indan-5-ol, in any enantiomeric form, or pharmaceutically acceptable ester or salt thereof, to the mammal.

10. The method according to claim 9, wherein the small mammal is a dog or a cat.

11. The method according to claim 9, which comprises administering from about 3 to about 30 µg of the 3-(1H-imidazol-4-ylmethyl)-indan-5-ol, in any enantiomeric form, or a pharmaceutically acceptable ester or salt thereof, to the mammal.

12. The method according to claim 11, wherein the small mammal is a dog or a cat.

13. A method for obtaining analgesia and anaesthesia in a mammal, which comprises administering to the mammal in need thereof an effective amount of an anesthetic, and intraspinally administering an effective amount of 3-(1H-imidazol-4-ylmethyl)-indan-5-ol, in any enantiomeric form, or a pharmaceutically acceptable ester or salt thereof, as an adjunct to the anaesthesia.

14. The method according to claim 13, wherein 3-(1H-imidazol-4-ylmethyl)-indan-5-ol hydrochloride is administered.

15. The method according to claim 13, wherein the 3-(1H-imidazol-4-ylmethyl)-indan-5-ol or pharmaceutically acceptable ester or salt thereof is administered intrathecally.

16. The method according to claim 13, wherein the 3-(1H-imidazol-4-ylmethyl)-indan-5-ol or pharmaceutically acceptable ester or salt thereof is administered epidurally.

17. The method according to claim 13, wherein the mammal is a human.

18. The method according to claim 17, which comprises administering from about 30 to about 500 µg of the 3-(1H-imidazol-4-ylmethyl)-indan-5-ol, or pharmaceutically acceptable ester or salt thereof, to the mammal.

19. The method according to claim 18, which comprises administering from about 50 to about 200 µg of the 3-(1H-imidazol-4-ylmethyl)-indan-5-ol, or pharmaceutically acceptable ester or salt thereof, to the mammal.

20. The method according to claim 1, which comprises treating intraoperative pain in the mammal.

21. The method according to claim 1, which comprises treating postoperative pain in the mammal.

22. The method according to claim 1, which comprises treating obstetric pain in the mammal.

23. The method according to claim 1, which comprises treating chronic pain in the mammal.

24. The method according to claim 1, which comprises treating spastic paraplegia in the mammal.

* * * * *